United States Patent [19]

Dolbeare et al.

[11] Patent Number: 4,812,394

[45] Date of Patent: * Mar. 14, 1989

[54] FLOW CYTOMERIC MEASUREMENT OF DNA AND INCORPORATED NUCLEOSIDE ANALOGS

[75] Inventors: Frank A. Dolbeare; Joe W. Gray, both of Livermore, Calif.

[73] Assignee: University of California, Berkeley, Calif.

[*] Notice: The portion of the term of this patent subsequent to Oct. 25, 2005 has been disclaimed.

[21] Appl. No.: 832,618

[22] Filed: Feb. 24, 1986

Related U.S. Application Data

[63] Continuation-in-part of Ser. No. 617,655, Jun. 5, 1984, Pat. No. 4,780,406, which is a continuation-in-part of Ser. No. 542,955, Oct. 18, 1983, Pat. No. 4,585,736.

[51] Int. Cl.[4] ............................................. C12Q 1/68
[52] U.S. Cl. ............................................. 435/6; 435/7; 435/29; 435/91; 435/810; 436/56; 436/63; 436/94; 436/508; 436/517; 436/518; 436/800; 935/77; 935/108
[58] Field of Search ............... 435/6, 7, 29, 91, 810; 436/63, 94, 56, 800, 508, 517, 518; 935/77, 108

[56] References Cited

PUBLICATIONS

Darzykiewicz et al., Exp. Cell Res., vol. 90, (1975), pp. 411–428.
Gratzner et al., J. Histochem. Cytochem., vol. 24, (1976), pp. 34–39.
Inman, Methods in Enz., vol. 29, (1974), pp. 451–458.
Darzykiewicz et al., J. Histochem. Cytochem., vol. 24, (1976), pp. 49–58.
Darzynkiewicz et al., J. Histochem. Cytochem., vol. 27, (1979), pp. 478–485.
Moran et al., J. Histochem. Cytochem., vol. 33, (1985), pp. 821–827.
Gratzner et al., Exp. Cell Res., vol. 95, (1975), pp. 88–94.
Gratzner et al., Cytometry, vol. 1, (1981), pp. 385–389.

*Primary Examiner*—Esther M. Kepplinger
*Assistant Examiner*—Stephen C. Wieder
*Attorney, Agent, or Firm*—Stephen C. Macevicz; Henry P. Sartorio

[57] ABSTRACT

A method is provided for simultaneously measuring total cellular DNA and incorporated nucleoside analog. The method entails altering the cellular DNA of cells grown in the presence of a nucleoside analog so that single stranded and double stranded portions are present. Separate stains are used against the two portions. An immunochemical stain is used against the single stranded portion to provide a measure of incorporated nucleoside analog, and a double strand DNA-specific stain is used against the double stranded portion to simultaneously provide a measure of total cellular DNA.

The method permits rapid flow cytometric analysis of cell populations, rapid identification of cycling and noncycling subpopulations, and determination of the efficacy of S phase cytotoxic anticancer agents.

39 Claims, 7 Drawing Sheets

FLOW CYTOMERIC MEASUREMENT OF DNA AND INCORPORATED NUCLEOSIDE ANALOGS

The United States Government has rights in this invention pursuant to Contract No. w-7405-ENG-48 between the U.S. Department of Energy and the University of California, for the operation of Lawrence Livermore National Laboratory.

This is a continuation-in-part of copending U.S. patent application, Ser. No. 617,655 filed June 5, 1984, which is a continuation-in-part of copending U.S. patent application, Ser. No. 542,955 filed Oct. 18, 1983, assigned to the same assignee and claims priority in said prior filed applications.

BACKGROUND OF THE INVENTION

The present invention relates generally to flow cytometry. More specifically, it relates to the simultaneous measurement of incorporated nucleoside analogs and the total cellular deoxyribonucleic acid (DNA) content by flow cytometric techniques.

A broad range of biological and biomedical investigations depends on the ability to distinguish cells that synthesize DNA from those that do not. Oncologists, for example, have devoted substantial effort to establishing correlations between the proportion of human tumor cells synthesizing DNA and treatment prognosis, e.g. Hart et al., *Cancer*, Vol. 39, pgs. 1603-1617 (1977). Effort has also been devoted to improvement of anti-cancer therapy with S-phase specific agents by treating when the experimentally determined proportion of tumor cells in S phase is maximal, e.g. Barranco et al., *Cancer Research*, Vol. 42, pgs. 2894-2898 (1982). In these studies, S-phase cells are usually assumed to be those that appear labeled in autoradiographs prepared immediately after pulse labeling with tritiated thymidine, or those with S-phase DNA content in DNA distributions measured flow cytometrically. Cancer researchers and oncologists have relied heavily on measurements of the proportion of DNA synthesizing cells to determine the cell cycle traverse characteristics of normal and malignant cells. The classical "fraction of labeled mitosis" procedure, Quastler et al., *Experimental Cell Research*, Vol. 17, pgs. 420-429 (1959), for example, depends on assessment of the frequency of mitotic cells that appear radioactively labeled in autoradiographs of samples taken periodically after labeling with tritiated thymidine. Studies of the cell cycle traverse characteristics of drug-treated cell populations typically require measurement of the amount of tritiated thymidine incorporated by cells in S phase (e.g., by liquid scintillation spectrometry) or determination of the fraction of cells with S-phase DNA content (e.g., by DNA distribution analysis), or both, Pallavicini et al., *Cancer Research*, Vol. 42, pgs. 3125-3131 (1982). Studies of mutagen-induced genetic damage that use unscheduled DNA synthesis as an index of damage also rely on the detection of low levels of incorporation of tritiated thymidine, e.g. Painter et al., *Biochim. Biophys. Acta*, vol. 418, pgs. 146-153 (1976).

These broad-ranging biomedical studies are often limited by the measurement techniques. For example, autoradiographic determination of the fraction of cells incorporating radioactive DNA precursors like tritiated thymidine is limited by the labor-intensive nature of the measurements and by the subjectivity associated with discrimination between unlabeled and weakly labeled cells, e.g. Simpson-Herren, et al., *Cancer Research*, Vol. 36, pgs. 4705-4709 (1976). Determination of the amount of radioactive DNA precursor incorporation by liquid scintillation is also suboptimal because no information is available about the distribution of radioactivity incorporation among the cells of the population. Finally, interpretation of DNA distributions measured by flow cytometry is difficult because no information is available about the absolute rate of DNA synthesis, Gray et al., in *Flow Cytometry and Sorting*, Melamed et al., Eds. (Wiley, New York, 1979) pgs. 383-407. Thus, a population proliferating with twice the rate of another might have the same DNA distribution if the two populations spend the same fractional times in the $G_1$, S, and $G_2M$ phases of the cell cycle. Furthermore, discrimination between actively synthesizing and quiescent cells with S-phase DNA content is impossible.

Recently several fluorometric procedures have been developed to overcome some of the limitations associated with techniques for detecting DNA synthesis that depend on incorporated radionucleotides. Darzynkiewicz and co-workers have attempted to distinguish non-cycling cells from cycling cells by the degree of denaturation of cellular DNA after treatment with acid. The degree of denaturation is measured by the dye acridine orange which emits green fluorescence upon intercalation into double stranded sections of the DNA, and which emits red fluorescence upon electrostatic binding to single stranded sections of DNA. Total cellular DNA is correlated to the sum of the intensities of red fluorescence and green fluorescence, Darzynkiewicz et al., "Thermal Denaturation of DNA In Situ as Studied by Acridine Orange Staining and Automated Cytofluorometry," *Experimental Cell Research*, Vol. 90, pgs. 411-428 (1975); and Darzynkiewicz et al., "Different Sensitivity of Chromatin to Acid Denaturation in Quiescent and Cycling Cells as Revealed by Flow Cytometry," *J. Histochem. Cytochem.*, Vol. 27, pgs. 478-485 (1979).

Latt et al., in "Flow cytometric analysis of bromodeoxyuridine - substituted cells stained with 33258 Hoechst," *J. Histochem Cytochem.*, Vol. 25, pg. 927 (1977), and later Noguchi et al., in "Measurement of DNA Synthesis by Flow Cytometry," *Cytometry*, Vol. 1, pgs. 390-393 (1981), have shown that the incorporation of bromodeoxyuridine (BrdU) can be detected flow cytometrically by its quenching effect on the fluorescence from the DNA-specific dye Hoechst 33258. This technique has been used to quantify the rates of cell cycle traverse by measuring Hoechst 33258 fluorescence distributions for cells grown continuously in medium containing BrdU, e.g. Bohmer, "Flow Cytometric Cell Cycle Analysis Using the Quenching of 33758 Hoechst Fluorescence by Bromodeoxyuridine Incorporation," *Cell and Tissue Kinetics*. Vol. 12, pgs. 101-110 (1979); and Rabinovitch, "Regulation of Human Fibroblast Growth Rate by Both Noncycling Cell Fraction and Transition Probability Is Shown by Growth in 5-Bromodeoxyuridine Followed by Hoechst 33258 Flow Cytometry," *Proc. Natl. Acad. Sci.* Vol. 80, pgs. 2951-2955 (1983). Phase durations were estimated from the rate at which cells with Gl-, S-, and G2M-phase DNA contents moved through S-phase, incorporated BrdU and showed reduced Hoechst 33258 fluorescence. Unfortunately, these studies required incorporation of substantial amounts of BrdU and would be difficult to conduct in vivo because of BrdU toxicity.

The utility of BrdU as a marker for proliferating cells has been substantially increased by the development of antibodies against BrdU incorporated into cellular DNA, botn polyclonal: Gratzner et al., "The Use of Antibody Specific for Bromodeoxyuridine for the Immunofluorescent Determination of DNA Replication in Single-Cells and Chromosomes, " *Experimental Cell Research,* Vol. 95, pgs. 88–94 (1975); and monoclonal: Gratzner, "Monoclonal Antibody to 5-Bromo-and 5-Iododeoxyuridine: A New Reagent for Detection of DNA Replication," *Science,* Vol. 218, pgs. 474–475 (1982); Gratzner, U.S. Pat. No. 4,529,700 issued 16 July 1985; Raza et al., "Rapid Enumeration of S-Phase Cells by Means of Monoclonal Antibodies, " *New England J. Medicine,* Vol. 310, pg. 991 (1984); and Vanderlaan et al., copending U.S. patent application Ser. No. 542,967 filed 18 Oct. 1983. when coupled with fluorescent labels the antibodies are highly sensitive reagents for measuring the amount of BrdU incorporated into cellular DNA. Use of the antibodies requires that native double stranded DNA be altered so that the bromodeoxyuridine moieties of the nucleic acid are made accessible to the antibodies. Such alteration is usually accomplished by disrupting the hydrogen bonds between the two strands of the native DNA by standard denaturing techniques, e.g. see Gratzner et al., *Experimental Cell Research,* Vol. 95, pgs. 88–94 (1975) in regard to a denaturation protocol used for appliction of anti-BrdU antibodies; and Henderson, *International Review of Cytology,* Vol. 76, pgs. 1–46, for an extensive review of denaturation protocols used in in situ hybridization studies. Unfortunately, use of the antibodies alone does not provide a means for correlating BrdU incorporation with the phases of the cell cycle, a measurement which would be highly useful in distinguishing cycling from non-cycling cells, in studies for quantifying cell cycle parameters, and also in the analysis of populations perturbed by anti-cancer agents.

SUMMARY OF THE INVENTION

Accordingly, it is an object of the subject invention to provide a simple method for resolving cellular DNA distribution in the three major phases of the cell cycle.

It is another object of the present invention to measure the level of incorporation of DNA precursors as a measure of DNA synthesis during the various phases of the cell cycle.

It is a further object of the instant invention to provide a flow cytometric technique for the simultaneous measurement of the total DNA content of a cell and the level of DNA synthesis during the various phases of the cell cycle.

It is an additional object of the present invention to provide a novel use for monoclonal antibodies reactive with DNA precursors in the measurement of DNA synthesis during various phases of the cell cycle with a simultaneous measurement of the total DNA content of the cell.

Yet another object of the present invention is to provide a method for the measurement of DNA synthesis following drug treatment in cancer therapy.

Still another object is to provide a method for the measurement of the rate of cell cycle traverse.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

Broadly the invention is a method for simultaneously measuring total cellular DNA and incorporated nucleoside analogs. The method is based on the discovery that whenever substantially the same proportion of DNA of each cell in a population is altered to make incorporated nucleoside analogs accessible to anti-analog antibodies, the following measurements are possible: staining the unaltered, or native double stranded, portions provides a measure proportional to total DNA content, and immunochemical staining of the altered portions of the DNA simultaneously, provides a measure proportional to the amount of incorporated nucleoside analogs. Thus, when such measurements are carried out on a population of cells, e.g. flow cytometrically, the measurement of unaltered DNA in a particular cell relative to the measurements recorded for a substantial portion of the population indicates the position of the cell in the cell cycle, e.g. by its relative position in a DNA histogram. At the same time, measurement of the amount of immunochemical stain attached to the altered DNA indicates whether and to what extent (relative to other cells in the population) DNA synthesis took place in the cell while exposed to a nucleoside analog, or some predetermined compound which is assimilated to form an incorporated nucleoside analog. The invention not only provides a means for detecting and measuring where in the cell cycle DNA synthesis occurs but it also provides a means for following an analog-labeled cohort as it progresses through the cell cycle.

An important application of the invention is a method for detecting drug resistant subpopulations of cells in an organism that has been treated with an S phase cytotoxic drug.

An important feature of the invention is the degree to which native or double stranded DNA is altered to permit access to incorporated nucleoside analogs by immunochemical stains. The portion of DNA altered for immunochemical staining must be large enough so that the attached immunochemical stain generates a measureable signal; conversely, the unaltered portion must also be large enough so that stains specific for that portion generate a measurable signal which allows $G_1$ phase cells to be distinguished from $G_2M$ phase cells. The precise numerical fraction of DNA altered in particular cases depends on several factors including (1) the nature of the immunochemical stain—its binding efficiency as well as the efficiency of its label in generating a signal, (2) the nature of the stain specific to unaltered DNA (referred to herein as the second stain), (3) the method of altering the DNA, and (4) the cell type being subjected to the measurements. Hereinafter, the altered portion of cellular DNA is referred to as the first portion, and the unaltered portion of the cellular DNA is referred to as the second portion. Cellular DNA can be altered in a variety of ways including, for example, strand separation, chemical modification of purine or pyrimidine bases, and enzymatic degradation of one of the two strands of the native DNA. Partial denaturation is a preferred means of altering cellular DNA to form a first portion and a second portion. As used herein denaturation refers to disrupting the interstrand hydrogen bonding of a native double stranded DNA molecule so that the double stranded molecule unwinds, or is separated, into separate single stranded sections. This process is sometimes referred to as melting. Partial denaturing as used herein refers to denaturing a portion of cellular DNA in a manner as described above; namely, the extent of denaturation must be consistent with the generation of signals from both mods of staining discussed above.

The method of the invention is applied to a population of cells by the following steps: growing the cells of the population in the presence of a predetermined compound, the predetermined compond being capable of assimilation into the DNA of the cells to form an incorporated nucleoside analog; altering a portion of the DNA of each cell of the population to substantially the same extent such that a first portion comprising altered DNA is formed and a second portion comprising unaltered DNA is formed, the first portion being sufficiently large so that it can be detected by an immunochemical stain specific for the incorporated nucleoside analog, and the second portion being sufficiently large so that it can be detected by a second stain specific thereto; applying the immunochemical stain to the cells; applying the second stain to the cells; and detecting at substantially the same time and for each cell of a substantial portion of the population, a first signal from the immunochemical stain bound to the first portion of DNA of each cell and a second signal from the second stain bound to the second portion of DNA of the same cell such that a first signal and a second signal is associated with each said cell of the substantial portion of the population.

As used herein the term "nucleoside analog" refers to a substitute for one of the four deoxyribo nucleosides—deoxyadenosine, deoxyguanosine, deoxycytidine, or deoxythymidine (the latter deoxyribo nucleoside also being referred to simply as thymidine)— making up DNA which is detectable by an immunochemical stain after the native DNA is appropriately altered. A nucleoside analog is an analog in the sense that DNA polymerase accepts its triphosphate derivative in place of the correct (i.e. with respect to the template nucleoside) triphosphate precursor during DNA synthesis, e.g. Bloch, Ed., "Chemistry, Biology, and Clinical Use of Nucleoside Analogs," *Annals of the New York Academy of Sciences*, Vol. 255 (1975). As used herein the term "incorporated nucleoside analog" refers to a nucleoside analog which has been integrated into the cellular DNA by the cell's synthetic machinery. Preferably the nucleoside analogs used with the invention are those which are non-toxic when incorporated into cellular DNA in detectable amounts. In particular, halodeoxyuridines are the preferred analogs of thymidine. More preferably, 5-chloro-, 5-bromo-, or 5-iododeoxyuridine are used as analogs of thymidine. And most preferably, 5-bromodeoxyuridine or 5-iododeoxyuridine are used as analogs of thymidine.

The term "predetermined compound" as used herein refers to the actual compound to which the cells are exposed while growing—whether in vivo or in vitro—which when assimilated by the cells results in the incorporation of nucleoside analogs.

The term "second stain" as used herein refers to a stain specific for tne unaltered, or second, portion of cellular DNA. Preferably the second stain is any stain which binds specifically to double stranded DNA. More preferably the second stain is an intercalating dye, and most preferably the intercalating dye is a fluorescent dye selected from the group consisting of ethidium bromide, propidium iodide, and acridine orange.

As used herein the term "immunochemical stain" refers to a composition for detecting a particular antigenic determinant wherein the composition includes antibodies—polyclonal or monoclonal—against the determinant. Moreover, the term comprehends a labeling means, or in other words, a means for generating the first signal, associated with the antibody. As explained more fully below, several different means are available for labeling the antibody. Preferably, the labeling means includes one or more fluorescent molecules for each anti-analog antibody. And preferably, the emission band of the fluorescent molecules is distinct from that of any DNA specific dye used to simultaneously stain the double stranded portions of the cellular DNA. That is, preferably the first signal, referred to above, is a fluorescent signal distinct from the second signal whenever it is fluorescent.

In reference to the population of cells whose DNA is simultaneously stained with an immunochemical stain and second stain, the term "substantial proportion" as used herein means that measurements must be carried out on a sufficiently large number of cells so that the cell cycle phase of individual cells can be determined by relative DNA content, e.g. by way of a standard DNA distribution obtained with a flow cytometer. It is also understood that cells of the substantial portion represent a random sample of the population.

The present invention addresses problems associated with detecting cells synthesizing DNA, and in measuring the extent to which such synthesis takes place and where in the cell cycle it takes place. The invention advantageously overcomes deficiencies in prior measurement techniques by simultaneously staining the cellular DNAs of a population of cells with two stains, one which provides a measure of total cellular DNA from which cell cycle phase can be determined, and another which provides a measure of the extent of DNA synthesis. Detection and/or measurement of the signals generated by the stains are carried out on populations of cells rapidly and efficiently by a flow cytometer.

The invention provides a means for determining the dose-response relationship between a particular tumor and S phase cytotoxic drugs. By establishing the minimum dose necessary to kill S phase cells, toxic side effects of the therapeutic agents can be minimized, and treatment protocols can be individualized.

BRIEF DESCRIPTION OF THE DRAWINGS

FIG. 1A was constructed from measurements on exponentially growing CHO cells prior to treatment with BrdU, and FIG. 1B was constructed from measurements or cells of the same population made immediately after a 30 minute exposure to BrdU at a concentration of 10 micromolar.

DETAILED DESCRIPTION OF THE PREFERRED EMBODIMENT

Figure 1B:
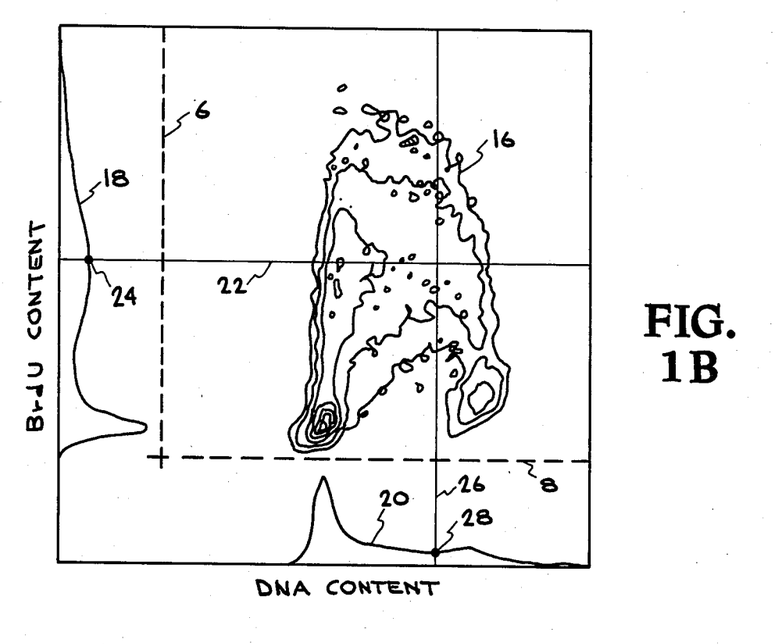
Figure 2A:
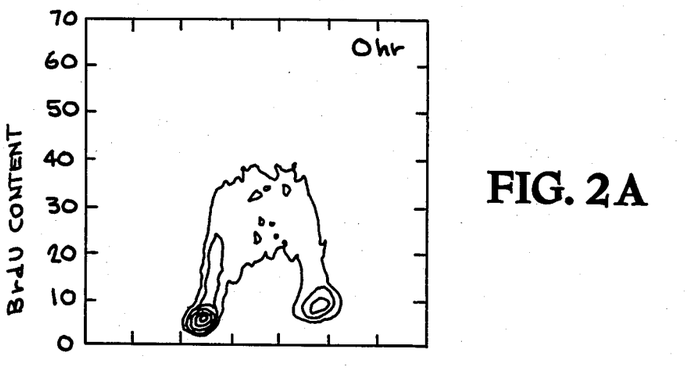
FIGS. 2A through 2F are contour plots of bivariate DNA-incorporated BrdU distributions derived from measurements on cell samples taken from an exponetially growing population of CHO cells at various times after a 30 minute exposure to BrdU at a concentration of 10 micromolars.

In accordance with the invention cells of a population are simultaneously stained with two stains such that a signal from one stain provides a measure of total cellular DNA, and a signal from the other simultaneously provides a measure of the amount of incorporated nucleoside analog. By measuring the amount of stain of each type on each cell of a substantial portion of the population, the fraction of DNA-synthesizing cells can be determined, and the location of the DNA-synthesizing cells in the cell cycle can be determined. One manner in which these determinations can be made is by constructing a contour plot from a record of the measurements on the individual cells, such as that shown in FIG. 1B, and which is discussed more fully below. In FIG. 1B the contour plot is indicated by 16. Dashed lines 6 and 8 represent the zero fluorescent lines for the stain against the incorporated nucleoside analog and the stain against unaltered DNA, respectively. Curves 18 and 20 represent the summation of all cells generating a given amount of fluorescence due to the staining of incorporated nucleoside analog, BrdU in this case, and unaltered DNA, respectively. For example point 24 on curve 18 represents the sum of all cells in contour plot 16 that lie on line 22, and point 28 on curve 20 represents the sum of all cells in contour plot 16 that lie on line 26. An important feature of the invention is the ability to obtain the data making up curve 20. Such data allows one to correlate cell cycle phase to the fluorescence measurement of the stain bound to the unaltered DNA using standard techniques, e.g. *Flow Cytometry and Sorting*, Melamed et al., Eds. (John Wiley & Sons, New York, 1979); cells indicating any incorporated BrdU above background are by definition S-phase cells (absent any factors causing aberrant DNA synthesis). Once cell cycle phase is correlated to position on contour plot 16, the distribution of BrdU incorporation over the cell cycle is readily determined. FIGS. 2A through 2F provide a dramatic illustration of how the invention allows one to track a cohort of cells labeled with BrdU as they progress through the cell cycle. FIG. 2A is roughly equivalent to FIG. 1B; they both result from measurements (made in accordance with the invention) on a population of cells that have been cultered in the presence of a nucleoside analog for a short period. The remaining FIGS. 2B through 2F, result from the same kind of measurements on the same population made at successive times after they have been removed from exposure to the nucleoside analog.

Preferably a flow cytometer is used to measure the fluorescence generated by the immunochemical stain and the stain against the unaltered portions of the cellular DNA. The principles and operation of such instruments are well-established, and several flow cytometers suitable for use with the invention are available commercially, e.g., *Flow Cytometry and Sorting*, Melamed et al., Eds. (John Wiley & Sons, New York, 1979); *Flow Cytometry; Instrumentation and Data Analysis*, Van Dilla et al., Eds. (Academic Press, New York, 1985); Mairhead et al., "Flow Cytometry: Present and Future," *Bio/Technology*, Vol. 3, pgs. 337–356 (1985); and U.S. Pat. Nos. 3,710,933; 3,380,584; and 4,325,706, which are incorporated by reference for their discriptions of flow cytometers. Other kinds of instruments such as those used in analytical cytology could also make the fluorescence measurements in accordance with the invention, albeit with less efficiency than flow cytometers, e.g. Ploem et al., "An Automated Microscope for Quantitative Cytology (Combining Television Image Analysis and Stage Scanning Microphotometry," *J. Histochem. Cytochem.*, Vol. 27, pgs 136–143 (1979).

Whenever flow cytometers are used, the method of the invention includes a step of preparing the cells for measurement on a flow cytometer. Basically the step requires that a single cell suspension be formed so that the flow cytometer's system for constraining the cells to flow single file past the excitation beams and detectors can be implemented. Preferably the cells are fixed, e.g., in 70 percent ethanol.

As mentioned above, an important feature of the invention is altering a portion of cellular DNA so that the anti-analog antibody of the immunochemical stain can gain access to the incorporated nucleoside analog. There are several ways in which the DNA can be altered to permit such access, e.g., Schreck et al, "Binding of Anti-Nucleoside Antibodies Reveals Different Classes of DNA in the Chromosomes of the Kangaroo Rat (*Dipodermys Ordii*), " *Experimental Cell Research*, Vol. 108, pgs. 403–411 (1977), where the generation of single stranded regions is accomplished by ultraviolet irradiation or by photo-oxidation after treatment with methylene blue. Preferably cellular DNA is altered enzmatically or, by standard denaturing agents, such as heat, acid, alkali, various organic reagents such as formamide, urea, formaldehyde, dimethyl sulfoxide, or tetralkylammonium halides.

Enzymatic alteration of cellular DNA can be carried out by a number of different commercially available enzymes, e.g. Boehringer Mannheim GmbH, Mannheim, FRG. Roughly the step involves randomly nicking the double stranded DNA with one enzyme, then stripping away single stranded sections with another to expose the incorporated nucleoside analogs. For example, nicking enzymes include DNase I (the standard nicking enzyme in the "nick translation" technique), and several restriction enzymes, including Bam HI and Pst I. "Stripping" enzymes include exonuclease III and T4 DNA polymerase (in the absence of nucleoside triphosphates).

An extensive literature has arisen on denaturing procedures using organic reagents in connection with electrophoresis, e.g., Maniatis et al., "Fractionation of Low Molecular Weight DNA or RNA in Polyacrylamide Gels Containing 98% Formamide or 7M Urea," *Methods in Enzymology*, Vol. 65, pgs. 299-305 (1980); biophysics, e.g. Marmur et al., "Denaturation of Deoxyribonucleic Acid by Formamide," *Biochim, Biophys. Acta.*, Vol. 51, pgs. 32-36 (1961); Brittin et al., "Analysis of Repeating DNA Sequences by Reassociation," *Methods in Enzymology*, Vol. 29, pgs. 363-418 (1974); Inman, "Denaturation Mapping of DNA," *Methods in Enzymology*, Vol. 29, pgs 451-458 (1974), or the like; and techniques for in situ hybridization, e.g. Henderson, *International Review of Cytology*, Vol. 76, pgs. 1-46 (1982), to name a few. Experience in these allied fields provides guidance for the application of denaturing agents in accordance with the invention.

The precise denaturing conditions used to bring about suitable partial denaturation in accordance with the invention depends on several factors including the nature of the cells on which the measurements are to be made. Consequently, some experimentation may be required for determining the optimal denaturing conditions for use on a particular cell type. For example, it has been found that mild acid treatment followed by thermal denaturation leads to the most sensitive detection of incorporated nucleoside analogs. However, for some cell types this treatment is too harsh, and cells are destroyed. The examples given below illustrate several representative partial denaturation protocols.

Preferably the partial denaturation step includes pretreatment with a mild acid, e.g. HCl at a concentration of about 0.1M, for about 10 minutes. It is believed that such pre-treatment extracts histones from the chromatin, and thereby causes the DNA to denature more readily and in a more uniform manner as between different cell types, e.g. Moran et al. "Detection of 5-Bromodeoxyuridine (BrdUrd) Incorporation by Monoclonal Antibodies: Role of the Denaturation Step," *J. Histochem Cytochem.*, Vol. 33, pgs. 821-827 (1985). Most preferably the cells are partially denatured following the mild acid treatment by heating with formamide.

Further examples of partial denaturation are disclosed by Darzynkiewicz in "Thermal Denaturation of DNA In Situ as Studied by Acridine Orange Staining and Automated Cytofluorometry," *Experimental Cell Research*, Vol. 90 pgs. 411-428 (1975), "Cytofluoromehic Studies on Conformation of Nucleic Acids In Situ: II. Denaturation of Deoxyribonucleic Acid," *J. Histochem Cytochem.*, Vol. 24, pgs. 49-58 (1976); and "Different Sensitivity of Chromatin to Acid Denaturation in Quiescent and Cycling Cells as Revealed by Flow Cytometry," *J. Histochem Cytochem.*, Vol. 27, pgs. 478-485 (1979).

The immunochemical stain of the invention comprises an antibody against the incorporated nucleoside analog (referred to as the anti-analog antibody) and a labeling means for generating a signal, i.e., the first signal referred to above. Many standard labeling means are available for use with the anti-analog antibody of the invention, and the selection of the best labeling means depends in part on the circumstances of the application, e.g., whether a flow cytometer is used, whether the cell type or preparative steps involved are compatible with its use, and the like, e.g., Hood et al., *Immunology* (Benjamin/Cummings Publishing Company, Menlo Part, 1978) pgs. 164-169 describes several methods of labeling antibodies including direct labels, indirect labels, and sandwich type labels. All such labels can serve as the labeling means of the immunochemical stain. The actual signal generated by the immunochemical stain can be based on fluorescence, absorption, radioactivity, or electron opacity of the labeling means. Preferably the labeling means generates a fluorescent signal. Techniques for constructing a fluorescent immunochemical stain, also referred to as an immunofluorescent stain, are well-known in the fields of cell biology, pathology, and medical diagnostics e.g. Higmans et al., Eds. "Fifth International Conference on Immunofluorescence and Related Staining Techniques," *Ann. N.Y. Acad. Sci.*, Vol. 254 (1975); and Haugland, *Molecular Probes: Handbook of Fluorescent Probes and Research Chemicals* (Molecular Probes, Inc., Junction City, 1985). Preferably, the immunochemical stain comprises a directly or indirectly fluorescently labeled anti-analog antibody. In both the direct and indirect means for labeling, the preferred fluorescent dyes are selected from the group consisting of fluorescein, Texas Red (a trade named product from Molecular Probes, Inc., Junction City, OR), tetramethylrhodamine, and phycoerythrin. These dyes are available commercially and are linked to the anti-analog antibodies by standard techniques, e.g. wood et al., *J. Immunol.*, Vol 95, pgs. 225-229 (1965); and Oi et al., *J. Cell Biol.*, Vol. 93, pgs. 981-986 (1982). At least two modes of indirect labeling are preferred: (1) The bound anti-analog antibody is reacted with a second directly labeled heterologous anti-immunoglobin antibody, and (2) the anti-analog antibody is covalently linked to one or more biotin molecules, the biotinylated antibody is reacted with the incorporated nucleoside analog and then the bound anti-analog antibody is reacted with directly labeled avidin. The avidin-biotin technique is well known, e.g. Bayer et al, "The use of the Avidin-Biotin Complex as a Tool in Molecular Biology," in Glide, Ed., *Methods of Biochemical Analysis*, Vol. 26, pgs. 1-45 (John Wiley, New York, 1980).

Another preferred labeling means includes linking an enzyme to an antibody in either the direct or indirect labeling scheme. The enzymes generate fluorescent or colorimetric products from colorless substrates. Preferred enzymes are alkaline phosphatase, beta-galactosidase, and peroxidase (most preferably horse radish peroxidase). The enzyme labeling techniques are also standard in the arts of cell biology and medicine, e.g. Kuhlmann, *Immuno Enzyme Techniques in Cytochemistry* (Verlag Chernie, Based, 1984); or Tijssen, *Practice and Theory of Enzyme Immunoassays* (Elsevier, New York, 1985).

Preferably the anti-analog antibody used in the invention is directed against incorporated halodeoxyuridines, particularly incorporated bromodeoxyuridine or iododeoxyuridine. For example, the antibodies disclosed by Gratzner, in U.S. Pat. No. 4,529,700, or by Vanderlaan et al., in U.S. patent application Ser. No. 542,967 filed 18 Oct. 1983, are suitable for use with the invention. Accordingly these references are incorporated by reference.

Preferably the stain specific for the unaltered portions of cellular DNA, i.e. the second stain, is a DNA specific fluorescent dye. The DNA specific dye can be intercalating or nonintercalating. Examples of nonintercalating dyes include Hoechst 33342 and 33258, mithramycin, chromomycin $A_3$, olivomycin, 4'-6-diamidino-2-phenylindole, and the like. Some of these dyes display higher affinities for adenosinethymidine base pairs, and others display higher affinities for guanosine-cytosine base pairs. Consequently, some loss of stoichiometry in the binding of the second stain could arise depending on the method used for altering the DNA. More preferably, the second stain is an intercalating fluorescent dye. And most preferably, the intercalating fluorescent dye is selected from the group consisting of ethidium bromide, propidium iodide; and acridine orange. Use of intercalating dyes to stain double stranded DNA (and RNA) is a well known technique, particularly in field of flow cytometry, e.g. Melamed, et al., *Flow Cytometry and Sorting* (John Wiley, New York, 1979); Krisham, "Rapid Flow Cytofluorometric analysis of Mammalian Cell Cycle by Propidium Iodide," *J. Cell Biol.*, Vol. 66, pgs. 188–193 (1975); "One-Step Ethidium Bromide DNA/Cell Staining Procedure," Ortho Instruments Protocol 28 (January 1979); and Taylor et al., "An Evaluation of DNA Fluorochromes, Staining Techniques, and Analysis for Flow Cytometry," *J. Histochem Cytochem*, Vol. 28, pgs 1224–1232 (1980); Steinkamp, *Rev. Sci. Instrum.*, Vol. 55, pgs 1375–1400 (1984); and Kruth, *Anal. Biochem.*, Vol. 125, pgs. 225–242 (1982); to name a few references on the subject. Some DNA specific dyes like propidium iodide bind to double stranded RNA as well as DNA. Preferably, whenever such dyes are used, cells are treated with RNAse before application of the dye using standard protocols, e.g., incubation for 20 minutes at 37° C. in PBS containing 1 mg/ml RNAse.

The following examples serve to illustrate the present invention. The concentration of reagents, temperatures, and values of other variable parameters are only to exemplify application of the present invention and are not to be considered as limitations thereof.

EXAMPLE I.

Chinese Hamster Ovary (CHO) Cells

CHO cells growing exponentially in minimal essential alpha medium (Gibco, Santa Clara, CA) with 10% fetal calf serum at $3 \times 10^5$ cells per ml were treated for 30 min with 10 micromolar BrdU. The cells were then refed with conditioned medium from a second untreated spinner flask. Twenty-milliliter aliquots were removed at 2-hr internals, counted, washed with phosphate-buffered saline (PBS), pH 7.2, and fixed for at least 30 minutes in cold 70% ethanol.

Cells were removed from ethanol (in which they can be stored for several days at 4° C.), and were partially denatured by resuspending in 2 ml of 1.5M HCl at 20° C. for 20 minutes, followed by two washings with 5 ml of PBS. Immunochemical staining was accomplished by resuspending the cells for 1 hour. In PBS containing 0.5 percent Tween 20 (Sigma Chemical Company, St. Louis), 0.5 percent bovine serum albumin, and 1:200 dilution of monoclonal antibody against BrdU (in particular the one disclosed by Gratzner in U.S. Pat. No. 4,529,700). Cells were then washed twice with PBS and resuspended for 30 minutes in PBS containing 0.5 percent Tween 20, a 1:100 dilution of a stock solution of fluorescein-labeled goat anti-mouse gamma globulin (Cappel Laboratories, Cochranville, PA), and 1 percent neutral goat serum (to prevent nonspecific adsorption of the fluorescein-labeled anti-mouse gamma globulin). The cells were then washed twice with 5 ml of PBS and resuspended in 1 ml of PBS containing 5 micrograms of propidium iodide (Polysciences, warington, PA) per ml.

After 1 hour, tee cells were ready for flow cytometric analysis.

During flow cytometry, cells were excited at 488 nm. Red fluorescence from propidium iodide was collected through a 600-nm-long wavelength pass filter and recorded as a measure of total DNA content and green fluorescence from fluorescein was collected through a 514-nm bandpass filter and recorded as a measure of the amount of incorporated BrdU. The resulting data were accumulated to form a bivariate $64 \times 64$ channel distribution showing the distribution of DNA (red fluorescence) and BrdU (green fluorescence) among the cells of the population.

Figure 1A:
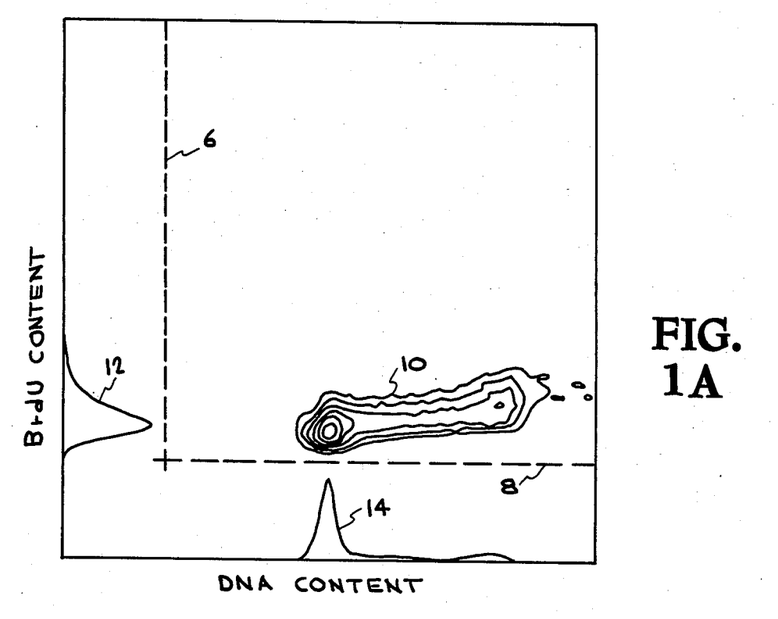
FIGS. 1A and 1B are contour plots of bivariate distributions illustrating the relative frequencies of cells with particular DNA content and amount of incorporated BrdU.

FIG. 1A is a contour plot of such a distribution based on measurements on the CHO population immediately prior to treatment with BrdU. FIG. 1B is a contour plot of a distribution based on measurements on the CHO population immediately after the 30 minute exposure to BrdU. The finite width of contour 10 and finite half width of curve 12 is due to nonspecific background fluorescence from the cells and/or nonspecific antibody binding in the cells. Fractions of cells in the various cell cycle phases are estimated by standard data analysis algorithms. The direct relationship between the intensity of fluorescent signal generated by the immunochemical stain and incorporated BrdU was verified by using tritiated BrdU in one set of experiments. Relative fluorescence intensity was then compared to relative radioactivity for selected cell fractions indicating a linear regression coefficient of about 0.97. Dolbeare et al. "Flow Cytometric Measurement of total DNA Content and Incorporated Bromodeoxyuridine," *Proc. Natl. Acad. Sci*, Vol. 80, pgs. 5573–5577 (1983) which discloses the results of the comparison is incorporated by reference.

Figure 2B:
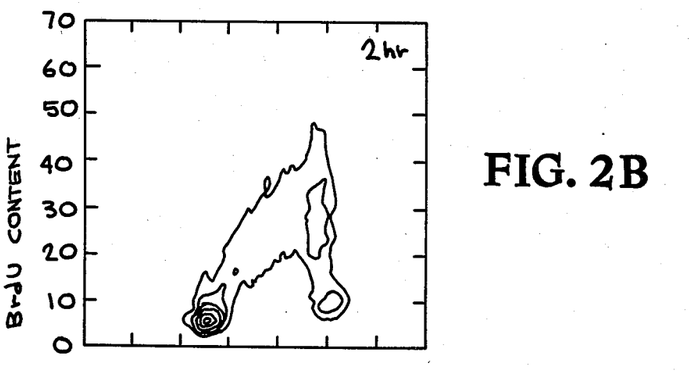
Figure 2C:
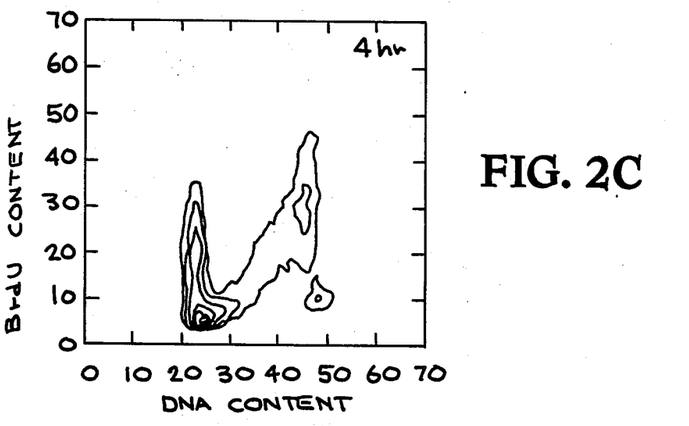
Figure 2D:
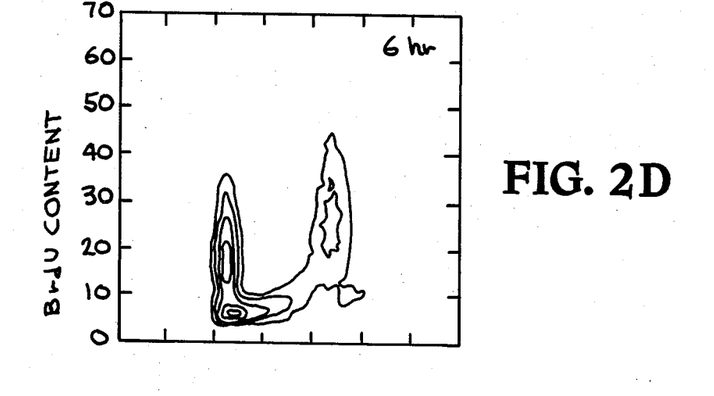
Figure 2E:
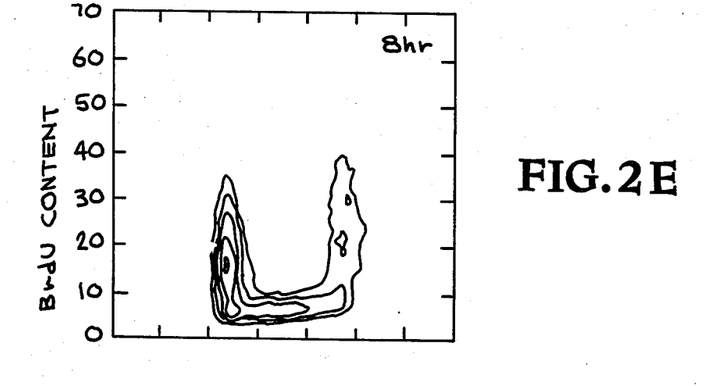
Figure 2F:
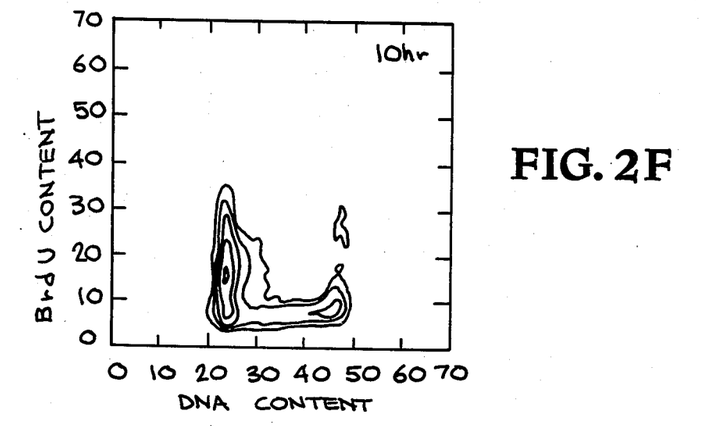

Cell cycle traverse rates were estimated from a sequence of bivariate DNA/incorporated BrdU distributions obtained from measurements made on population samples taken periodically after exposure to BrdU. FIGS. 2A through 2F are contour plots of such distributions which correspond to measurements on samples taken at the indicated times after exposure to BrdU. These data show that the BrdU-labeled cohort, initially in S-phase (FIG. 2A), begins to move out of S phase and through G2M immediately after labeling (FIG. 2B). By 8 hours, the labeled cells are predominantly in G2M phase and G1 phase (FIG. 2C through 2E), and by 10 hours they have begun to reenter S phase (FIG. 2F). The $G_1$-, S- and $G_2M$- phase durations for the CHO cells were estimated to be 7.2, 7.4, and 1.1 hours, respectively, using standard data analysis techniques, e.g. Gray et al. "Rapid Cell Cycle Analysis by Measurement of the Radioactivity Per Cell in a Narrow Window in S Phase ($RCS_i$)," *Cell Tissue Kinet.*, Vol. 10, pgs. 97–109 (1977); or Yanagisawa et al., "Cell cycle Analysis Using Numberical Simulation of Bivariate DNA/Bromodeoxyurdine Distributions," *Cytometry*, Vol. 6, pgs. 550–562 (1985).

Alternatively, CHO cells can be partially denatured by incubating at an elevated temperature in the presence of formamide. There is roughly a direct relationship between each of the following variables and the extent of denaturation: formamide concentration, temperature, and duration of treatment. The following sets of denaturing conditions resulted in suitable partial denaturation of CHO cellular DNA: (1) 80° C. for 30 minutes in formamide having a concentration (by volme) in PBS in the range of between about 40–80 percent; (2) incubating at a temperature in the range of between about 65-90° C., for 30 minutes in 50% formamide; and (3) 80° C. for between about 30-80 minutes in 50% formamide.

EXAMPLE II.

Drug-Treated C3H Mice.

Control and drug-treated (cytosine arabinoside) female C3H mice (obtained from washington Univeristy, St. Louis, MO) were injected intraperitoneally with 50 mg of BrdU per Kg 1 hour prior to sacrifice. Drug-treated mice received BrdU 3, 6, and 9 hours after a single intraperitoneal injection of 500 mg cytosine arabinoside (Upjohn) per Kg. The femurs of each mouse were removed and the hematopoietic cells were harvested by flushing with 1 ml of alpha medium. The recovered cells were then resuspended by pipeting, filtered through 37-micrometer mesh, and fixed with 70% elthanol. Cellular DNA was partially denatured and stained as described in Example I.

Figure 3A:
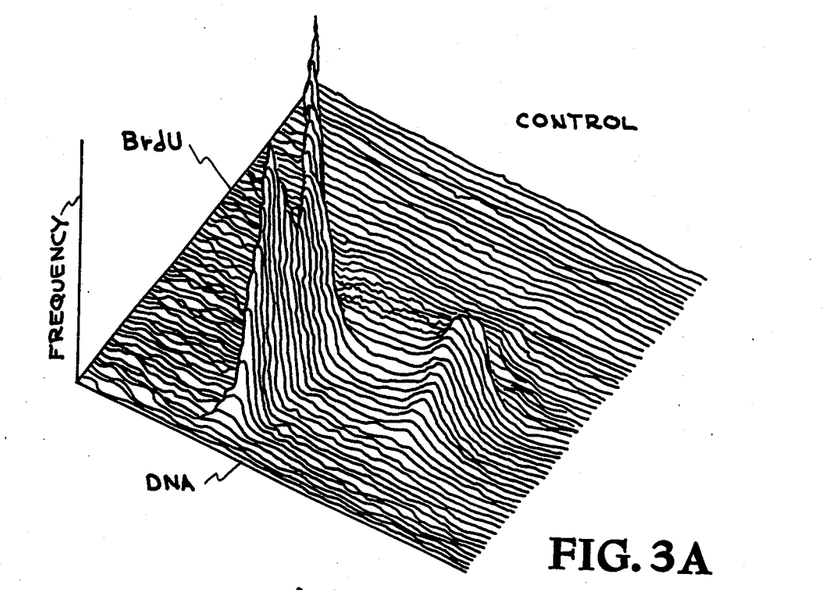
FIG. 3A is a bivariate DNA-incorporated BrdU distribution of measurements on bone marrow cells from a control mouse pulse labeled with BrdU.
Figure 3B:
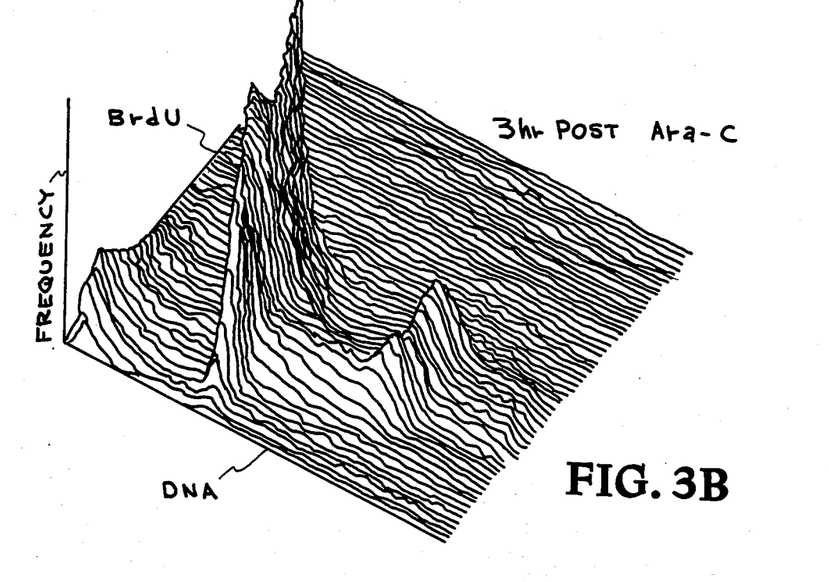
FIGS. 3B through 3D are bivariate DNA-incorporated BrdU distributions of mouse bone marrow cells obtained from mice pulse labeled with BrdU at various times after treatment with cytosine arabinoside (Ara-C).
Figure 3C:
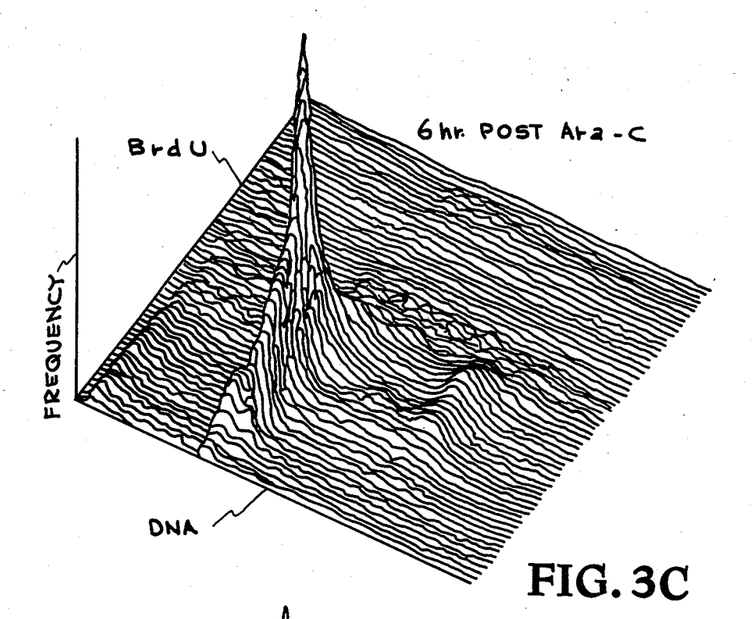
Figure 3D:
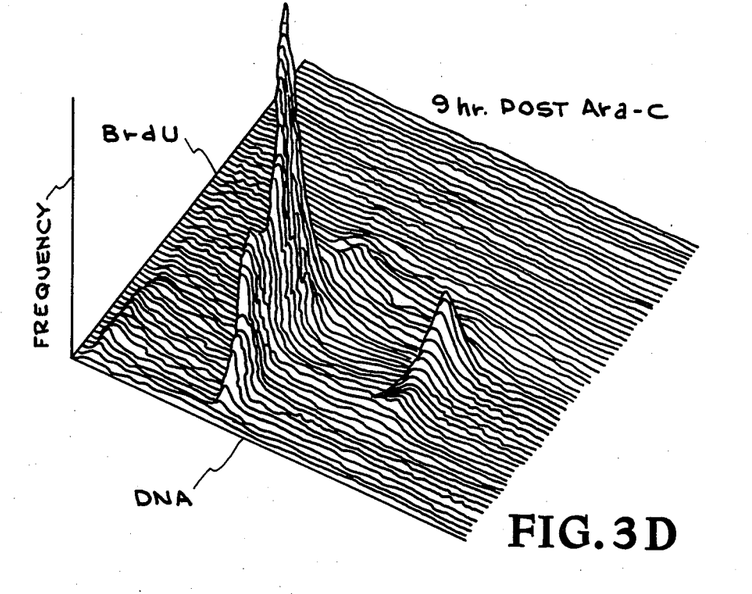

FIGS. 3B through 3D shows bivariate DNA-Incorporated BrdU distributions measured for the mouse bone marrow cells obtained from mice pulse labeled with BrdU 3, 6, and 9 hours after treatment with 500 mg of cytosine arabinoside per Kg. The control distribution (FIG. 3A) was obtained from mice that received only BrdU 30 minutes prior to sacrifice.

EXAMPLE III

KHT Tumor Cells

The KHT sarcoma is a transplantable murine solid tumor initially described by Kallman et al., "Factors Influencing The Quantitative Estimation of the In Vivo Survival of Cells from Solid Tumors," *J. Natl. Cancer Inst.*, Vol. 39, pgs. 539-549 (1967). Procedures for maintenance of this tumor and it dispersal into a single cell suspension are described in Pallavicini et al., "Solid KHT Tumor Dispersal for Flow Cytometric Analysis," *Cytometry*, Vol. 2, pgs. 54-58 (1981), which is incorporated by reference. Briefly, the KHT tumors were carried in C3H/He female mice 10-12 weeks of age (Bantan and Kingman, Fremont, CA). Mice were injected i.p. with BrdU (50 mg/kg) in physiological saline 30 minutes prior to sacrifice by $CO_2$ asphyxiation. Tumors were harvested when the tumor had grown to approximately 0.6 g, and were disaggregated with neutral protease (Sigma, St. Louis, MO) to form a single cell suspension. The disaggregated cells were washed in PBS and fixed in cold 70% ethanol.

Approximately two million ethanol fixed cells were sedimented, resuspended in 1.5 ml PBS containing RNAse (1 mg/ml), and incubated for 20 minutes at 37° C. The cells were sedimented and resuspended in cold 0.1M HCl for 10 minutes, sedimented, and partially denatured by incubating in 50% formamide (by volume in PBS) at 80° C. for 30 minutes. Alternatively, the cells can be partially denatured by incubating in distilled water for 10 minutes at 100° C. (with slightly increased cell loss). Partially denatured cells were resuspended in 5 ml PBS (pH 7.2) containing 0.5% bovine serum albumin, 0.5% Tween 20 (this three component mixture hereinafter being referred to as augmented PBS), and monoclonal anti-BrdU (from hybridoma IU-2 described by Vanderlaan et al., in copending U.S. patent application Ser. No. 542,967 filed 18 Oct. 1983) diluted 1 to 1000 (approximately 2 micrograms per ml IgG final antibody concentration). After 30 minutes at 25° C., 5 ml augmented PBS was added, the cells were sedimented, were washed once in augmented PBS and were resuspended in 200 microliters of goat anti-mouse IgG-FITC (Sigma Chemical Company, St. Louis, MO) dissolved in augmented PBS. After 20 minutes at 25° C., 5 ml of augmented PBS was added, the cells were sedimented, were washed once in augmented PBS, and were resuspended in 1.5 PBS containing 5 micrograms/ml propidium iodide. The cells were ready for flow cytometric analysis after 5 minutes.

EXAMPLE IV

L1210 Mouse Leukemia Cells: Detection of Drug-Resistant Subpopulations

This example demonstrates the operability of the invention for detecting resistant subpopulations of cells when such cells comprise 1% or less of the total population. The example demonstrates that the invention can be used to determine dose-response relationships between tumors and S phase cytotoxic drugs. That is, the amount of nucleoside analog incorporation, BrdU in this example, becomes an inverse measure of tumor sensitivity to a particular dose of drug, e.g. as determined by concentration and exposure time. Generally, after tumor cells are treated with an S phase cytotoxic drug, they are pulse labeled with the nucleoside analog (or predetermined compound).

Two L1210 mouse leukemia cell lines were obtained from DCT Tumor Bank (worcester, MA). One cell line was sensitive to and the other line resistant to cytosine arabinoside (Ara-C). Both L1210 cell lines were cultured in vitro in minimum essential medium (Gibco, Santa clara, CA) supplemented with 10% fetal calf serum. They were subcultured twice weekly and reestablished in fresh medium at about $5 \times 10^4$ cells per ml.

Both lines exhibited a doubling time of 11-13 hours in vivo and in vitro. Cells were grown in vivo as ascites tumors in DBA/2 mice (Simonsen, Gilroy, CA), greater than nine weeks old and weighing 20-25g. Mice were inoculated intra-peritoneally with $10^5$ cells by injection of 0.2 ml of $10^6$ cells/ml PBS (137 mM NaCl, 2.7 mM KCl, 4.3 mM $N_2PHO_4-7H_2O$, 1.5 mM $KH_2PO_4$) suspension on day 0. Ascites tumor cells were harvested on day 5 by peritoneal lavage. Mice were sacrificed by cervical dislocation, abdomens were swabbed with alcohol, and abdominal skin was incised and separated from the underlying peritoneum. Ten ml of ice cold PBS was injected into the peritoneal cavity through an 18 gauge needle, and then reaspirated into the syringe. Cells were pelleted and resuspended in cold 70% ethanol for fixation.

Staining was accomplished as follows. Approximately $10^7$ cells were pelleted from ethanol and incubated in 1.0 mg/ml RNase A (Worthington) in PBS at 37 degrees C. for fifteen minutes. Cells were then pelleted and resuspended in 1.5 ml ice cold 0.1M HCl, and left on ice for ten minutes. The cells were then washed once and resuspended in 2.0 ml distilled water. This suspension was placed in boiling water for 10 minutes and then rapidly cooled on ice. Cells were pelleted, resuspended in 0.30 ml anti-BrdU monoclonal antibody (produced by hybridoma IU-1 described by Vanderlaan et al. in copending U.S. patent application Ser. No. 542,967 filed 10 Oct. 1983) diluted 1:1000 in augmented PBS and incubated 30 minutes at room temperature. Cells were washed twice with 5.0 ml of wash buffer (0.5% Tween 20 in PBS), resuspended in 0.30 ml FITCconjugated goat anti-mouse antibody (Sigma) diluted 1:100 in augmented PBS and incubated 20 minutes at room temperature. Cells were again washed twice with wash buffer and resuspended in 1.5 ml 10 microgram/ml propidium iodide in PBS. Cells were ready for flow cytometric analysis after one hour.

Figure 4A:
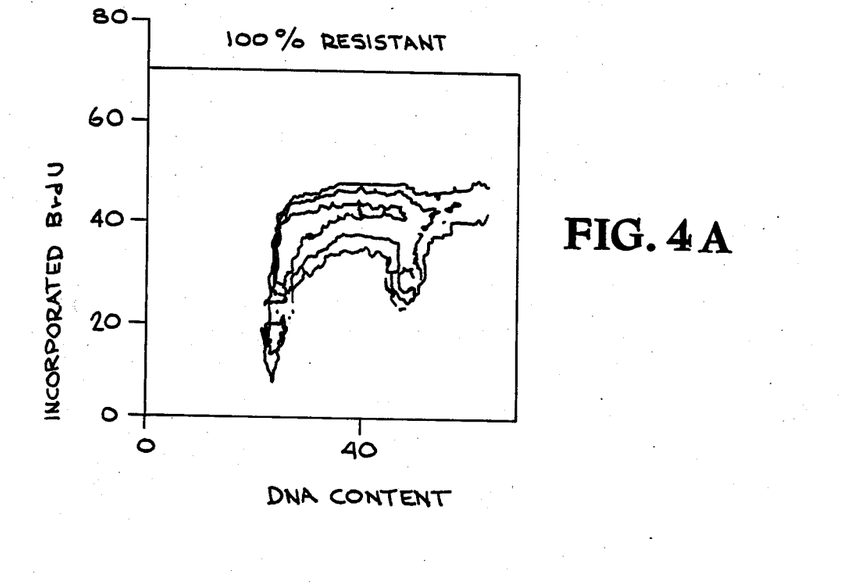
FIG. 4A is a contour plot of a DNA-incorporated BrdU distribution obtained from an in vitro population of Ara-C resistant L1210 leukemia cells after treatment with Ara-C followed by pulse labeling with BrdU.
Figure 4B:
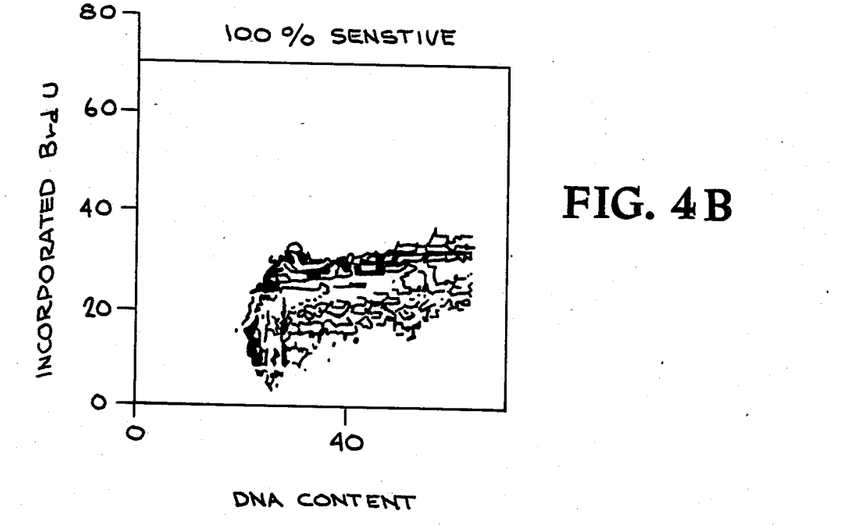
FIG. 4B is a contour plot of a DNA-incorporated BrdU distribution obtained from an in vitro population of Ara-C sensitive L1210 leukemia cells after treatment with Ara-C followed by pulse labeling with BrdU.
Figure 4C:
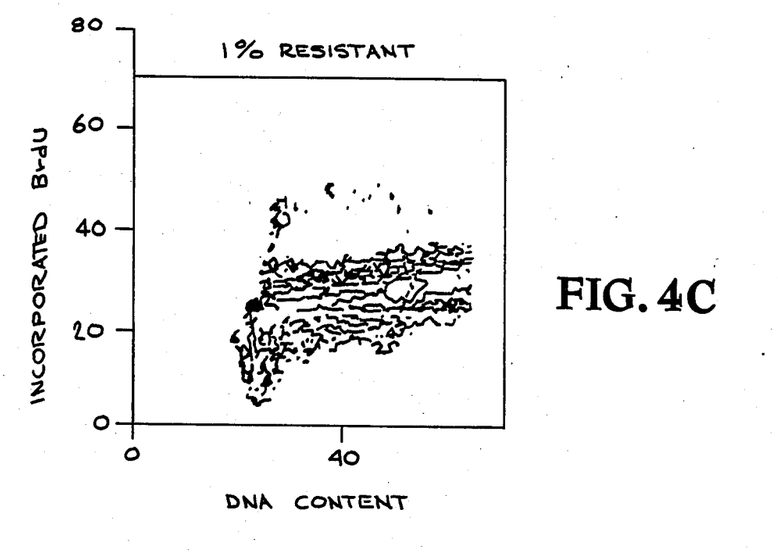
FIG. 4C is a contour plot of a DNA-incorporated BrdU distribution obtained from a mixed in vivo population of Ara-C resistant and Ara-C sensitive cells whose starting ratio was 1:100, respectively. The cells were treated with AraC then pulse labeled with BrdU before harvesting.
Figure 4D:
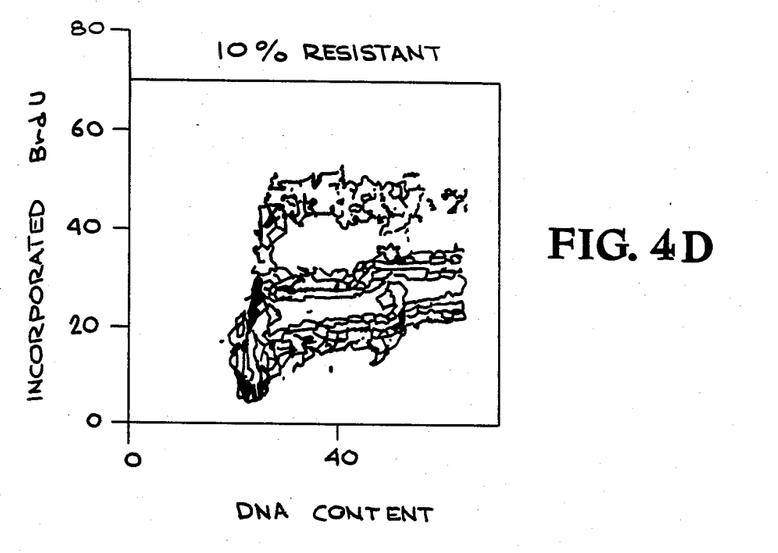
FIG. 4D is a contour plot of a DNA-incorporated BrdU distribution obtained from a mixed in vivo population of Ara-C resistant and Ara-C sensitive cells whose starting ratio was 1:10, respectively. The cells were treated with Ara-C then pulse labeled with BrdU before harvesting.

FIG. 4A is a contour plot of a DNA-incorporated BrdU distribution obtained from an in vivo culture of the Ara-C resistant L1210 cells. FIG. 4B is the analogous contour plot for the Ara-C ensitive L1210 cells. FIGS. 4C and 4D are contour plots of DNA-incorporated BrdU distributions from in vivo cultures of mixtures of the sensitive and resistant strains whose starting inoculations were 1% and 10% resistant to sensitive, respectively. The mice from which the cells were obtained were treated as follows. Populations of $2 \times 10^5$ cells were injected i.p. into each mouse. On day 5, Ara-C was injected i.p. at 2.5 mg/kg. After 30 minutes, BrdU was injected i.p. at 50 mg/kg. Cells were harvested 30 minutes after the BrdU injection.

EXAMPLE V.

Denatoration with Nucleases

KHT tumor cells or CHO cells were grown in the presence of BrdU and fixed as in Examples I and III. The fixed cells were sedimented, resuspended in 1.5 ml. PBS containing RNAse (1 mg/ml), and incubated for 20 minutes at 37° C.. Next the cells were sedimented resuspended, and incubated for 10 minutes in a solution containing cold 0.1M HCl and 0.7% Triton X-100. The cells were then sedimented and washed with 5 ml PBS, resuspended, and incubated for 30 minutes in 50 microliters of nuclease buffer (250 units of Bam HI, 33 millimolar Tris-acetate, 66 millimolar potassium acetate, 10 mililmolar magnesium acetate, 1 mg/ml bovine serum albumin, and 0.5 millimolar mercaptoethanol), after which 5 microliters of Exonuclease III (approximately 200 units) was added. After incubation for 60 minutes, 5 ml of PBS containing 0.5% Tween-20 was added, and the cells were sedimented. The sedimented cells were then stained, and analyzed flow cytometically as in the examples above.

The foregoing description of the preferred embodiments and examples of the subject invention have been presented for purposes of illustration and description and for a better understanding of the invention. They are not intended to be exhaustive or to limit the invention to the precise forms disclosed; and obviously, many modifications and variations are possible in light of the above teaching. The particular examples were chosen and described in some detail to best explain the principles of the invention and its practical application to thereby enable others skilled in the relevant art to best utilize the invention in various embodiments and with various modifications as are suited to the particular use contemplated. It is intended tnat the invention be defined by the claims appended hereto.

We claim:

1. A non-radioactive method for measuring unaltered cellular DNA and incorporated nucleoside analog, the method comprising the steps of:
   growing a population of cells in the presence of a non-radioactive predetermined compound, the non-radioactive predetermined compound being capable of assimilation into the DNA of the cells of the population to form an incorporated nucleoside analog whose presence can be detected by an immunochemical stain;
   altering a portion of the DNA of each cell of the population to substantially the same extent such that a first portion comprising altered DNA is formed and a second portion comprising unaltered DNA remains, the first portion being sufficiently large so that nucleoside analogs incorporated therein can be detected by an immunochemical stain specific for the incorporated nucleoside analog, and the second portion being sufficiently large so that $G_1$ phase cells of the population can be distinguished from the $G_2M$ phase cells of the population by a second signal generated by a second stain specific for the second portion;
   applying the immunochemical stain to the cells;
   applying the second stain to the cells; and
   detecting at substantially the same time and for each cell of a substantial portion of the population, a non-radioactive first signal from the immunochemical stain bound to the incorporated nucleoside analog in the first portion of DNA of each cell and a second signal from the second stain bound to the second portion of DNA of the same cell such that a first signal and a second signal are associated with each said cell of the substantial portion of the population.

2. The method of claim 1 wherein said step of altering includes enzymatically degrading single stranded portions of said DNA of each cell of said population such that the complementary strands of the degraded portions remain substantially intact to form said first portion of said cellular DNA.

3. The method of claim 1 wherein said step of altering includes partially denaturing said DNA of each cell of said population.

4. The method of claim 3 wherein said second stain is a DNA specific fluorescent dye.

5. The method of claim 4 wherein said step of detecting includes measuring flow cytometrically said first signal and said second signal substantially simultaneously.

6. The method of claim 5 wherein said immunochemical stain comprises an anti-analog antibody conjugated directly to a fluorescent dye.

7. The method of claim 6 wherein said fluorescent dye of said immunochemical stain is selected from the group consisting of fluorescein, Texas Red, tetramethylrhodamine, and phycoerythrin.

8. The method of claim 7 wherein said incorporated nucleoside analog is selected from the group consisting of 5-chlorodeoxyuridine, 5-bromodeoxyuridine, and 5-iododeoxyuridine.

9. The method of claim 8 wherein said incorporated nucleoside analog is 5-bromodeoxyuridine or 5-iododeoxyuridine.

10. The method of claim 9 wherein said DNA specific fluorescent dye is an intercalating dye selected from the group consisting of propidium iodide, ethidium bromide, and acridine orange.

11. The method of claim 6 wherein said step of partially denaturing includes treating said cells with concentrated acid.

12. The method of claim 11 wherein said concentrated acid is hydrochloric acid at a concentration in the range of between about 1.5 to 4.0 molar.

13. The method of claim 12 wherein said incorporated nucleoside analog is selected from the group consisting of 5-chlorodeoxyuridine, 5-bromodeoxyuridine, and 5-iododeoxyuridine.

14. The method of claim 13 wherein said incorporated nucleoside analog is 5-bromodeoxyuridine or 5-iododeoxyuridine.

15. The method of claim 14 wherein said DNA specific fluorescent dye is propidium iodide or Hoechst 33258 and said fluorescent dye conjugated to said anti-analog antibody is selected from the group consisting of fluorescein, tetramethylrhodamine, Texas Red, and phycoerythrin.

16. The method of claim 6 wherein said step of partially denaturing includes heating said cells.

17. The method of claim 16 wherein said step of partially denaturing includes heating said cells in the presence of an organic solvent selected from the group consisting of formamide, formaldehyde, urea, dimethyl sulfoxide, and tetraethylammonium hydroxide.

18. The method of claim 17 wherein said organic solvent is formamide at a concentration within the range of between about 35 to 80 percent.

19. The method of claim 18 wherein said incorporated nucleoside analog is selected from the group consisting of 5-chlorodeoxyuridine, 5-bromodeoxyuridine, and 5-iododeoxyuridine.

20. The method of claim 19 wherein said incorporated nucleoside analog is 5-bromodeoxyuridine or 5-iododeoxyuridine.

21. The method of claim 20 wherein said step of applying said immunochemical stain includes treating said cells with a mild acid so that nuclear proteins are extracted.

22. The method of claim 21 wherein said step of treating said cells includes treating in hydrochloric acid at a concentration in the range of between about 0.08 to 0.2 molar for about 5 to 15 minutes.

23. The method of claim 22 wherein said DNA specific fluorescent dye is propidium iodide or Hoechst 33258 and said fluorescent dye conjugated to said anti-analog antibody is selected from the group consisting of fluorescein, tetramethylrhodamine, Texas Red, and phycoerythrin.

24. A method for detecting a subpopulation of drug-resistant cells after treatment with a cytotoxic drug capable of inhibiting DNA synthesis, the method comprising the steps of:

exposing the drug treated cells to a predetermined compound, the predetermined compound being capable of assimilation into the DNA of the drug treated cells whenever they are synthesizing DNA to form an incorporated nucleoside analog;

altering a portion of the DNA of each cell of a population of drug treated cells to substantially the same extent such that a first portion of cellular DNA comprising altered DNA is formed and a second portion of cellular DNA comprising double stranded DNA remains, the first portion being sufficiently large so that nucleoside analogs incorporated therein can be detected by an immunochemical stain specific for the incorporated nucleoside analog, and the second portion being sufficiently large so that $G_1$ phase cells of the population can be distinguished from $G_2M$ phase cells of the population by a second signal generated by a second stain specific for the second portion;

applying the immunochemical stain to the cells;

applying the second stain to the cells;

detecting at substantially the same time and for each cell of a substantial portion of the population of drug treated cells, a first signal from the immunochemical stain bound to the incorporated nucleoside analogs in the first portion of DNA of each cell and the second signal from the second stain bound to the second portion of DNA of the same cell such that a first signal and a second signal is associated with each said cell of the substantial portion of the population of drug treated cells; and detecting the subpopulation of drug-resistant cells by identifying cells in the population of drug treated cells having S phase DNA content whose associated first signal indicates that nucleoside analog has been incorporated during S-phase.

25. The method of claim 24 wherein said immunochemical stain comprises an anti-analog antibody conjugated directly to a fluorescent dye, and wherein said second stain is a DNA specific fluorescent dye.

26. The method of claim 25 wherein said step of altering includes enzymatically degrading single stranded portions of said DNA of each cell of said population such that the complementary strands of the degraded portions remain substantially intact to form said first portion of said cellular DNA.

27. The method of claim 25 wherein said step of altering includes partially denaturing said DNA of each cell of said population.

28. The method of claim 27 wherein said incorporated nucleoside analog is 5-bromodeoxyuridine or 5-iododeoxyuridine.

29. The method of claim 28 wherein said step of partially denaturing includes heating said cells.

30. The method of claim 29 wherein said step of partially denaturing includes heating said cells in the presence of formamide at a concentration within the range of between about 35 to 80 percent.

31. The method of claim 30 wherein said DNA specific fluorescent dye is propidium iodide or Hoechst 33258 and said fluorescent dye conjugated directly to said anti-analog antibody is selected from the group consisting of fluorescein, tetramethylrhodamine, Texas Red, and phycoerythrin.

32. A kit for measuring unaltered cellular DNA and incorporated nucleoside analog in a population of cells previously exposed to a predetermined compound capable of being assimilated into the DNA of the cells of the population to form the incorporated nucleoside analog, the kit including containers of each reactant comprising:

an effective amount of an immunological stain specific for the incorporated nucleoside analog;

an effective amount of a second stain specific for the double stranded portions of the DNA of the cells; and an effective amount of DNA altering agent.

33. The kit of claim 32 wherein said DNA altering agent is formamide having a concentration by volume in phosphate buffered saline in the range between about 35–80 percent.

34. The kit of claim 33 further including a container of an effective amount of pretreatment acid.

35. The kit of claim 34 wherein said pretreatment acid is hydrochloric acid at a concentration of about 0.1M.

36. The kit of claim 32 wherein said DNA altering agent comprises an effective amount of a double stranded DNA nicking enzyme and an effective amount of an exonuclease.

37. The kit of claim 36 wherein said exonuclease is exonuclease III.

38. The kit of claim 37 further including a container of an effective amount of pretreatment acid.

39. The kit of claim 38 wherein said pretreatment acid is hydrochloric acid at a concentration of about 0.1M.

* * * * *